US009875664B2

(12) United States Patent
Dalal et al.

(10) Patent No.: US 9,875,664 B2
(45) Date of Patent: Jan. 23, 2018

(54) VIRTUAL TRAINER OPTIMIZER METHOD AND SYSTEM

(71) Applicant: Xerox Corporation, Norwalk, CT (US)

(72) Inventors: Edul N. Dalal, Webster, NY (US); Wencheng Wu, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 521 days.

(21) Appl. No.: 14/293,593

(22) Filed: Jun. 2, 2014

(65) Prior Publication Data

US 2015/0348429 A1    Dec. 3, 2015

(51) Int. Cl.

| G09B 5/06 | (2006.01) |
|---|---|
| G09B 19/00 | (2006.01) |
| A61B 5/11 | (2006.01) |
| A61B 5/00 | (2006.01) |
| A61B 5/0205 | (2006.01) |
| A61B 5/08 | (2006.01) |
| A61B 5/024 | (2006.01) |
| A61B 5/021 | (2006.01) |

(52) U.S. Cl.
CPC .............. G09B 5/06 (2013.01); A61B 5/0077 (2013.01); A61B 5/1114 (2013.01); A61B 5/1123 (2013.01); A61B 5/1128 (2013.01); G09B 19/003 (2013.01); A61B 5/021 (2013.01); A61B 5/02055 (2013.01); A61B 5/02416 (2013.01); A61B 5/0816 (2013.01); A61B 5/1117 (2013.01); A61B 5/486 (2013.01); A61B 5/744 (2013.01); A61B 2505/09 (2013.01); A61B 2576/00 (2013.01)

(58) Field of Classification Search
CPC ....................................... G09B 5/06

USPC ......................................... 434/258
See application file for complete search history.

(56) References Cited

U.S. PATENT DOCUMENTS

| 8,582,811 | B2 | 11/2013 | Wu et al. | |
|---|---|---|---|---|
| 8,600,213 | B2 | 12/2013 | Mestha et al. | |
| 8,617,081 | B2 | 12/2013 | Mestha et al. | |
| 2012/0271143 | A1* | 10/2012 | Aragones | G06F 19/3481 600/407 |
| 2012/0289850 | A1 | 11/2012 | Xu et al. | |
| 2013/0033484 | A1 | 2/2013 | Liao et al. | |
| 2013/0076913 | A1 | 3/2013 | Xu et al. | |
| 2013/0077823 | A1 | 3/2013 | Mestha et al. | |
| 2013/0218028 | A1 | 8/2013 | Mestha | |
| 2013/0322729 | A1 | 12/2013 | Mestha et al. | |
| 2013/0324876 | A1 | 12/2013 | Bernal et al. | |

(Continued)

OTHER PUBLICATIONS

X. Zhu, D. Ramanan, "Face Detection, Pose Estimation and Landmark Localization in the Wild", Computer Vision and Pattern Recognition (CVPR) Providence, Rhode Island, Jun. 2012, 8 pages.

(Continued)

*Primary Examiner* — Robert P Bullington
(74) *Attorney, Agent, or Firm* — Fay Sharpe LLP

(57) ABSTRACT

This disclosure provides an augmented Virtual Trainer (VT) method and system. According to an exemplary system, a video based physiological metric system is integrated with a VT system to provide health and/or safety related data associated with a user of the VT system. According to an exemplary embodiment, the disclosed augmented VT system modifies an exercise routine based on the physiological metrics and/or provides audio signals to the user.

20 Claims, 5 Drawing Sheets

(56) References Cited

U.S. PATENT DOCUMENTS

2013/0342756 A1 12/2013 Xu et al.
2013/0345568 A1 12/2013 Mestha et al.
2015/0125832 A1* 5/2015 Tran .................. G09B 5/00
434/127

OTHER PUBLICATIONS

U.S. Appl. No. 13/710,974, filed Dec. 11, 2012, Liu et al.
Erik E. Stone and Marjorie Skubic, "Evaluation of an Inexpensive Depth Camera for Passive In-Home Fall Risk Assessment", 2011, 5th International Conference on Pervasive Computing Technologies for Healthcare (PervasiveHealth) and Workshops, 7 pages.
"JointType Enumeration", 3 pages, http://msdn.microsoft.com/en-us/library/microsoft.kinect.jointtype.aspx, Dec. 5, 2013.
"Kinect for Windows Sensor Components and Specifications", http://msdn.micorsoft.com/en-us/library/jj131033.aspx, 2 pages, Mar. 14, 2014.
"Sensor Setup", http://www.microsoft.com/en-us/kinectforwindows/purchase/sensor_setup.aspx, 2 pages, Mar. 13, 2014.
"Kinect", http://en.wikipedia.org/wiki/Kinect, 17 pages, Mar. 14, 2014.
IBISWorld, "Physical Therapists Market Research Report", 2013, 2 pages.
http://en.wikipedia.org/wiki/Dynamic_time_warping, 4 pages.

* cited by examiner

VIRTUAL TRAINER OPTIMIZER METHOD AND SYSTEM

CROSS REFERENCE TO RELATED PATENTS AND APPLICATIONS

U.S. patent application Ser. No. 14/293,325, filed Jun. 2, 2014, by Edul N. Dalal et al. and entitled "HYBRID PERSONAL TRAINING SYSTEM AND METHOD" is incorporated herein by reference in its entirety.

BACKGROUND

There are many types of fitness training, including weight training, calisthenics, yoga, Pilates, aerobic dancing such as Zumba®, etc. Regardless of the type of fitness training, two characteristics are essential: (a) proper "form", i.e., the way in which the exercise is performed; and (b) proper exertion level, i.e., number of repetitions, intensity and/or duration of the workout, etc. Proper form and optimum exertion level maximize the benefit of the exercise, while poor form and sub-optimal exertion level result in an inefficient workout, wasting time and effort. Even more importantly, poor form and/or excessive exertion level can lead to serious injuries which may require medical treatment, loss of work, or permanent disability, in addition to pain and suffering.

Physical therapy (PT) is a health care profession which deals with the treatment of physical impairments and disabilities which may be caused by injury, disease or congenital disorders. It provides improved mobility and functional ability, including greater strength and dexterity. Fitness training is similar, but is intended primarily for nominally healthy individuals. For the purposes of this disclosure, the differences between physical therapy and general fitness training are not significant, and are therefore considered interchangeably.

The ultimate level of a fitness program is personal training, wherein a skilled personal trainer works with a client to implement a customized fitness training program. One of the most important functions of a personal trainer is to pay close attention to the form, as well as the exertion level, of the individual client's workout. However, expert personal trainers can be very expensive, due, in part, to extensive and frequent repetition of a routine.

At the other end of the scale, an alternative option is to perform a workout following generic instructions from a pre-recorded video. Such videos can be purchased on DVD relatively inexpensively. In this case there is no customization and, in particular, there is no inspection for proper form or exertion level, with consequent low efficiency and the risk of injury as mentioned earlier.

A recent development is something referred to as a Virtual Trainer (VT), which combines an animated or recorded video instruction method, combined with a video analytic approach. A VT system analyzes the form of a subject exerciser in terms of pose and compares it to that of an instructed form, i.e., exercise, and points out discrepancies to the exerciser in a variety of ways. Examples include Nike+ Kinect® Training, Dance Central® 3, Adidas miCoach®, and NBA® Baller Beats. All of these are available for the XBOX 360® and use a built-in Kinect® structured light depth measurement system to track the motions of an exerciser and thereby compare the exerciser's form to that of a pre-recorded instruction. However, because a VT system does not have a human trainer inspecting the exerciser's form, the ability to truly personalize the instruction to the exerciser is limited.

A good personal trainer is well aware of the exertion level of an exerciser, and adjusts the workout suitably to keep it at an optimum level. If the exerciser is allowed to perform at a lower exertion level than optimum, his/her progress in terms of fitness metrics will be significantly decreased. On the other hand, performing at a higher exertion level than optimum can be dangerous to the health and safety of the exerciser, and in extreme cases can be deadly. A major shortcoming of current VT systems is that they are unable to determine, and therefore to optimize, the exerciser's exertion level.

Even among normal people, optimum exertion levels can vary widely, and may be much lower than that of a professional athlete. Moreover, many exercisers participate in exercise programs as treatment for health conditions such as obesity, diabetes, hypertension, etc., where optimum exertion levels may be significantly lower than that of ordinary people in normal health.

What is needed is a VT system which can provide an optimum exertion level of an exerciser at appropriate times, similar to the service of a good personal trainer.

INCORPORATION BY REFERENCE

U.S. Pat. No. 8,617,081, by Mestha et al., issued Dec. 31, 2013 and entitled "Estimating Cardiac Pulse Recovery from Multi-Chanel Source Data via Constrained Source Separation";

U.S. Pat. No. 8,600,213, by Mestha et al., Issued Dec. 3, 2013, and entitled "Filtering Source Video Data via Independent Component Selection";

U.S. Pat. No. 8,582,811, by Wu et al., issued Nov. 12, 2013, and entitled "Unsupervised Parameter Settings for Object Tracking Algorithms";

U.S. Patent Publication No. 2013/0345568, by Mestha et al., published Dec. 26, 2013, and entitled "Video-Based Estimation of Heart Rate Variability";

U.S. Patent Publication No. 2013/0342756, by Xu et al., published Dec. 26, 2013, and entitled "Enabling Hybrid Video Capture of a Scene Illuminated with Unstructured and Structured Illumination Sources";

U.S. Patent Publication No. 2013/0324876, by Bernal et al., published Dec. 5, 2013, and entitled "Processing a Video for Tidal Chest Volume Estimation";

U.S. Patent Publication No. 2013/0322729, by Mestha et al., published Dec. 5, 2013, and entitled "Processing a Video for Vascular Pattern Detection and Cardiac Function Analysis";

U.S. Patent Publication No. 2013/0218028, by Mestha, published Aug. 22, 2013, and entitled "Deriving Arterial Pulse Transit Time from a Source Video Image";

U.S. Patent Publication No. 2013/0077823, by Mestha et al., published Mar. 28, 2013, and entitled "Systems and Methods for Non-Contact Heart Rate Sensing";

U.S. Patent Publication No. 2013/0076913, by Xu et al., published Mar. 28, 2013, and entitled "System and Method for Object Identification and Tracking";

U.S. Patent Publication No. 2013/0033484, by Liao et al., published Feb. 7, 2013, and entitled "System and Method for Interactive Markerless Paper Documents in 3D Space with Mobile Cameras and Projectors";

U.S. Patent Publication No. 2012/0289850, by Xu et al., published Nov. 15, 2012, and entitled "Monitoring Respiration with a Thermal Imaging System";

U.S. patent application Ser. No. 13/710,974, by Liu et al., filed Dec. 11, 2012, and entitled "Methods and Systems for Vascular Pattern Localization Using Temporal Features";

X. Zhu, D. Ramanan. "Face Detection, Pose Estimation and Landmark Localization in the Wild", Computer Vision and Pattern Recognition (CVPR) Providence, R.I., June 2012, 8 pages;

Erik E. Stone and Marjorie Skubic, "Evaluation of an Inexpensive Depth Camera for Passive In-Home Fall Risk Assessment", 2011, 5th International Conference on Pervasive Computing Technologies for Healthcare (PervasiveHealth) and Workshops, 7 pages;

"JointType Enumeration", 3 pages, Dec. 5, 2013;

"Kinect for Windows Sensor Components and Specifications", 2 pages, Mar. 14, 2014;

"Sensor Setup", 2 pages, Mar. 13, 2014;

IBISWorld, "Physical Therapists Market Research Report", 2013, 2 pages;

"Dynamic Time Warping", 4 pages; and

"Kinect", 17 pages, Mar. 14, 2014, are incorporated herein by reference in their entirety.

BRIEF DESCRIPTION

In one embodiment of this disclosure, described is a computer implemented virtual training (VT) method comprising: communicating via one or both of video and audio instructions for performing an exercise routine to a user of a VT system, the exercise routine to be performed by the user; sensing exercise motion of the user using one or more sensing elements, the sensing elements including an image capturing device acquiring an image of the user; processing an image of the user to determine an exertion level of the user during performance of the exercise routine, and based on the determined exertion level of the user, performing one of the following: a) communicating to the user one or more instructions which increase the exertion level; b) communicating to the user one or more instructions which decrease the execution level; or c) communicating to the user one or more instructions which maintain exertion level.

In another embodiment of this disclosure, described is a virtual training (VT) system comprising: a controller configured to execute instructions to perform a virtual training method, and one or more sensing elements operatively associated with the controller, the virtual training method comprising: communicating via one or both of video and audio instructions for performing an exercise routine to a user of a VT system, the exercise routine to be performed by the user; sensing exercise motion of the user using one or more sensing elements, the sensing elements including an image capturing device acquiring an image of the user; processing an image of the user to determine an exertion level of the user during performance of the exercise routine, and based on the determined exertion level of the user, performing one of the following: a) communicating to the user one or more instructions which increase the exertion level; b) communicating to the user one or more instructions which decrease the execution level; or c) communicating to the user one or more instructions which maintain exertion level.

In still another embodiment of this disclosure, described is a computer program product comprising: a non-transitory computer-usable data carrier storing instructions that, when executed by a computer, cause the computer to perform a virtual training method comprising: communicating via one or both of video and audio instructions for performing an exercise routine to a user of a VT system, the exercise routine to be performed by the user; sensing exercise motion of the user using one or more sensing elements, the sensing elements including an image capturing device acquiring an image of the user; processing an image of the user to determine an exertion level of the user during performance of the exercise routine, and based on the determined exertion level of the user, performing one of the following: a) communicating to the user one or more instructions which increase the exertion level; b) communicating to the user one or more instructions which decrease the execution level; or c) communicating to the user one or more instructions which maintain exertion level.

DETAILED DESCRIPTION

This disclosure provides a method and system of augmenting the capabilities of a virtual training system by using audio output and video input to detect unsafe conditions for the users and, then, to dynamically modify the exercise routine to prevent accidents or other health related incidents and/or simply provide a warning to the user. According to one exemplary embodiment, a virtual trainer is built on an Xbox® platform which contains all of the hardware necessary to implement the augmented training method and system according to this disclosure. In addition, the disclosed Virtual Trainer (VT) may include open source software to locate and track important body parts such as the face or joints in order to have image analysis software process those parts of the image which may indicate problems related to breathing, poor balance, or pain associated with facial features. Even though the body is moving, the system can still track these important features and the data can be used to dynamically modify the exercise routine to match the user's particular situation to keep them in the sweet spot for safety and correct physical exertion. The analysis can take into account a specific exercise routine that is being used so that recommendations can align with the intended goals of that routine. In other words, the disclosed virtual training method and system integrates health awareness with Virtual Trainers.

Figure 1:
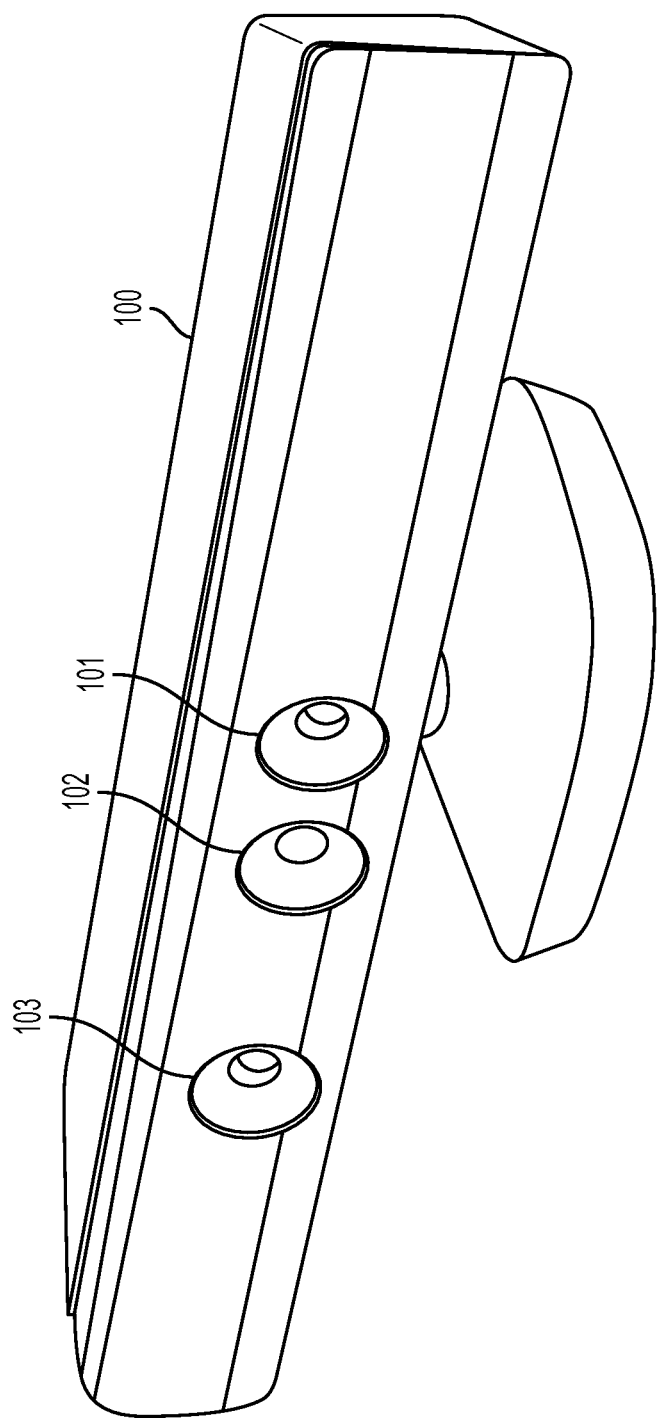
FIG. 1 is an exemplary embodiment of a video capturing system according to this disclosure.

With the advent of the Microsoft® Kinect® sensor, see FIG. 1, which provides low cost, depth capable, open source data acquisition, many new applications have been quickly brought to the market with minimal development effort. Since this disclosure and the exemplary embodiments provided herein leverage these benefits, a brief description of relevant features provided by Kinect® is given here. Beyond the raw imaging capability of acquiring RGB and depth videos, Kinect® also offers various capabilities in human body-part identification and tracking.

Embodiments of the disclosure can be integrated into or be in tandem with a camera system 100 that can involve a depth-sensing range camera, an infrared structured light source and a regular RGB color camera, as shown in the camera system 100 of FIG. 1. The depth-sensing camera 101 can approximate distances of objects by continuously projecting and interpreting reflected results from the structured infrared light source 103. The depth camera yields a so-called depth image, which is precisely aligned with the images captured by the RGB camera 102 to create a RGB and depth (RGBD) image. Thus embodiments of the disclosure can determine the depth of each pixel in the color images, establish a three-dimensional coordinate system with respect to the RGB camera, and transform each coordinate into real world coordinates. The RGB camera may also be utilized to identify content or features of an identified surface, so that when gestures are made, the RGB camera can detect the gestures within the identified surface with respect to the identified content.

Figure 2:
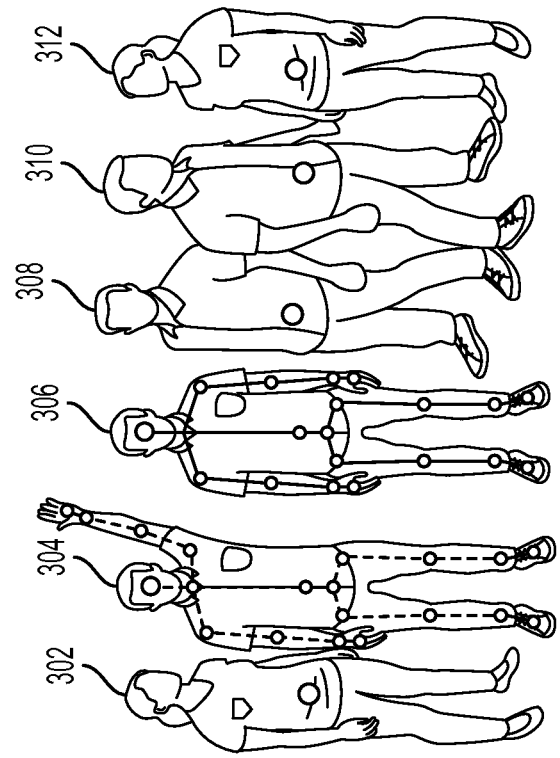
FIG. 2 illustrates twenty body joints detected by KINECT®.
Figure 3:
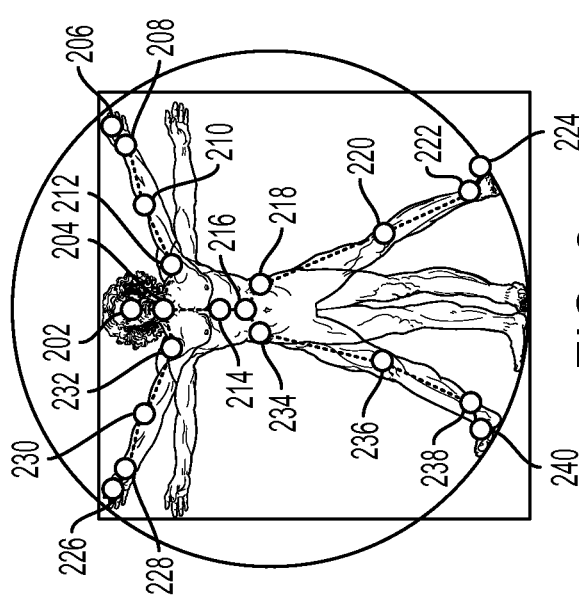
FIG. 3 illustrates person/body-part tracking capability of KINECT®.

Beyond the raw imaging capability of acquiring RGB and depth (RGBD) videos, Kinect® also offers various capabilities in human body-part identification and tracking. FIG. 2 illustrates twenty body-joints detected by the open source Kinect® tool, which includes head 202, shoulder center 204, left hand 206, left wrist 208, left elbow 210, shoulder left 212, spine 214, hip center 216, hip left 218, left knee 220, left ankle 222, left foot 224, right hand 226, right wrist 228, right elbow 230, shoulder right 232, hip right 234, right knee 236, right ankle 238 and right foot 240. See "JointType Enumeration", 3 pages, Dec. 5, 2013, for more detail. FIG. 3 illustrates the human/human-part tracking offered by open source Kinect® tool. As shown in FIG. 3, the Kinect® sensor, as-is, can track up to 2 persons 304 and 306 with full human body-part tracking, plus up to 4 additional persons, 302, 308, 310 and 312. These features are more than enough to implement a Hybrid training method and system as described in this disclosure.

Provided herein is a method and system to enable a VT system to be aware of the exertion level of a given exerciser at a given time, so that the VT system can adjust the workout so an exerciser will perform at an optimum exertion level. Moreover, much of this can be done without any additional hardware requirements above what is provided by a Kinect® sensor.

More specifically, the disclosed VT system is an exertion level and safety inspection system that works alongside a virtual trainer system to achieve an optimum exertion level. The exertion level inspection system determines cardio-respiratory performance characteristics, such as respiration and heart rate, and optionally more advanced metrics such as body temperature, blood pressure and heart rate variation of the exerciser, and determines whether the exertion level, i.e., speed and intensity of exercises, number of repetitions, etc., should be increased or decreased to maintain an optimum exertion level. The optimum exertion level may be determined using information specific to the given exerciser. Simple exerciser-specific information may include, for example, age, where a commonly-used value of the predicted maximum heart rate is given by (220−age). Corrections to this heart rate value may be made for factors such as gender, health condition, etc., and may also include input from the exerciser's physician or healthcare provider. If advanced exertion metrics such as blood pressure are used, there is a reduced need for exerciser-specific information. In such cases, actual maximum heart rate values may be determined independently. Significant depression of actual maximum heart rate below predicted maximum heart rate can then be used to alert the exerciser and/or their healthcare provider of latent health problems.

In addition to the detection of cardio-respiratory performance characteristics, the disclosed system can also detect anomalies/accidents such as falls, and optionally alert a care-giver and/or notify the authorities.

The method and system described herein can be combined with a monitoring function to provide a valuable service. While monitoring a service can be useful for people in normal health, it can provide critical assistance to vulnerable people such as those who are elderly and/or have chronic health conditions, e.g., diabetes, obesity, hypertension, coronary disease, etc., and/or are recovering from an injury or surgery. Exercise is a critical factor in the care of such vulnerable people, but their exertion level must be carefully monitored and controlled. However, supervised exercise facilities are expensive and often inaccessible to many people who need it. Moreover, they are also less likely to be able to exercise at a gym due to cost, mobility, comfort level, etc., and exercising unsupervised at home can be dangerous for some people.

Figure 4:
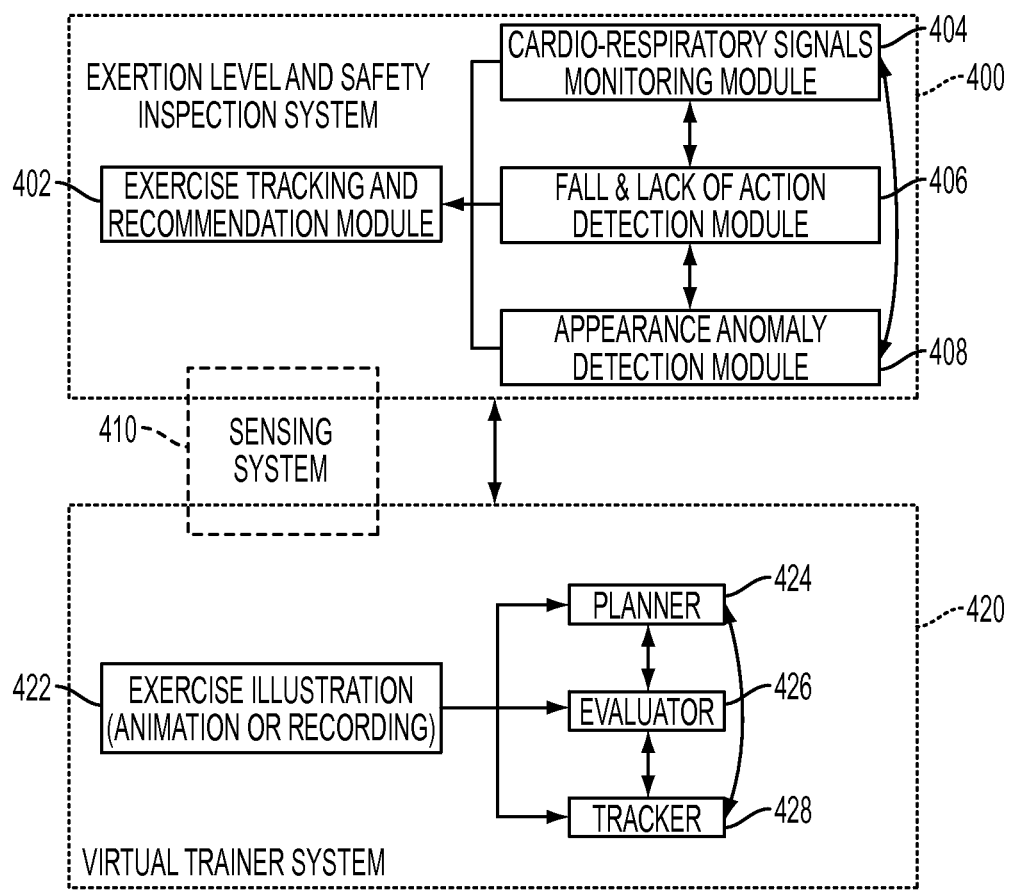
FIG. 4 is a block diagram of an augmented VT system according to an exemplary embodiment of this disclosure.

An overview of an exemplary embodiment of an augmented VT system according to this disclosure is illustrated in FIG. 4, where an Exertion Level and Safety Inspection System 400 share a common sensing system 410 used by a VT system 420. The Exertion Level and Safety Inspection System 400 is controlled by a central control unit, i.e., an Exercise Tracking and Recommendation Module Control 402, which receives inputs from at least one of a Cardio-Respiratory Signals Monitoring Module 404, a Fall and Lack of Action Detection Module 406, and an Appearance Anomaly Detection Module 408. Furthermore, the Exertion Level and Safety Inspection System 400 communicates with a VT system 420 to determine the appropriate exertion level of the exerciser as well as take appropriate precautions/actions if an unexpected event is observed.

The various modules comprising the disclosed augmented VT system are further described below.

Cardio-Respiratory Signals Monitoring (CRSM) Module 404.

Recent advances in video-based methods for detecting and monitoring physiological parameters, e.g., cardio-respiratory signals of humans, provide for the detection and/or monitoring of various human physiological conditions via regular RGB video camera/webcam under a somewhat controlled, i.e., cooperative, environment. See U.S. Pat. No. 8,617,081, by Mestha et al., issued Dec. 31, 2013 and entitled "Estimating Cardiac Pulse Recovery from Multi-Chanel Source Data via Constrained Source Separation"; U.S. Pat. No. 8,600,213, by Mestha et al., Issued Dec. 3, 2013, and entitled "Filtering Source Video Data via Independent Component Selection"; U.S. Patent Publication No. 2013/0345568, by Mestha et al., published Dec. 26, 2013, and entitled "Video-Based Estimation of Heart Rate Variability"; U.S. Patent Publication No. 2013/0342756, by Xu et al., published Dec. 26, 2013, and entitled "Enabling Hybrid Video Capture of a Scene Illuminated with Unstructured and Structured Illumination Sources"; U.S. Patent Publication No. 2013/0324876, by Bernal et al., published Dec. 5, 2013, and entitled "Processing a Video for Tidal Chest Volume Estimation"; U.S. Patent Publication No. 2013/0322729, by Mestha et al., published Dec. 5, 2013, and entitled "Processing a Video for Vascular Pattern Detection and Cardiac Function Analysis"; U.S. Patent Publication No. 2013/0218028, by Mestha, published Aug. 22, 2013, and entitled "Deriving Arterial Pulse Transit Time from a Source Video Image"; U.S. Patent Publication No. 2013/0077823, by Mestha et al., published Mar. 28, 2013, and entitled "Systems and Methods for Non-Contact Heart Rate Sensing"; U.S. Patent Publication No. 2012/0289850, by Xu et al., published Nov. 15, 2012, and entitled "Monitoring Respiration with a Thermal Imaging System"; and U.S. patent application Ser. No. 13/710,974, by Liu et al., filed Dec. 11, 2012, and entitled "Methods and Systems for Vascular Pattern Localization Using Temporal Features". As an example, a video heart-rate monitoring system recently developed works by first locating a facial region of a subject, collecting temporal color signals averaged over a region of interest of the detected face, and analyzing segments of the temporal color signals to yield a heart rate over time. This system is quite accurate if the subject remains reasonably still over the course of the measurement and the frontal view of the face is acquired.

A typical workout environment conducted by a VT system, e.g., use of Nike$_+$ Kinect® Training, although not exactly like the above-mentioned controlled environment, is still relatively constrained and predictable. It is thus possible to monitor an exerciser's heart-rate and other cardio-respiratory signals if the following information is taken into account: (1) location of the face (2) the pose of the face, i.e., frontal or not, and (3) distance of the face to the sensor, which are readily available from Kinect® with its ability to detect and track up to 20 body-joints of the exerciser.

Figure 5:
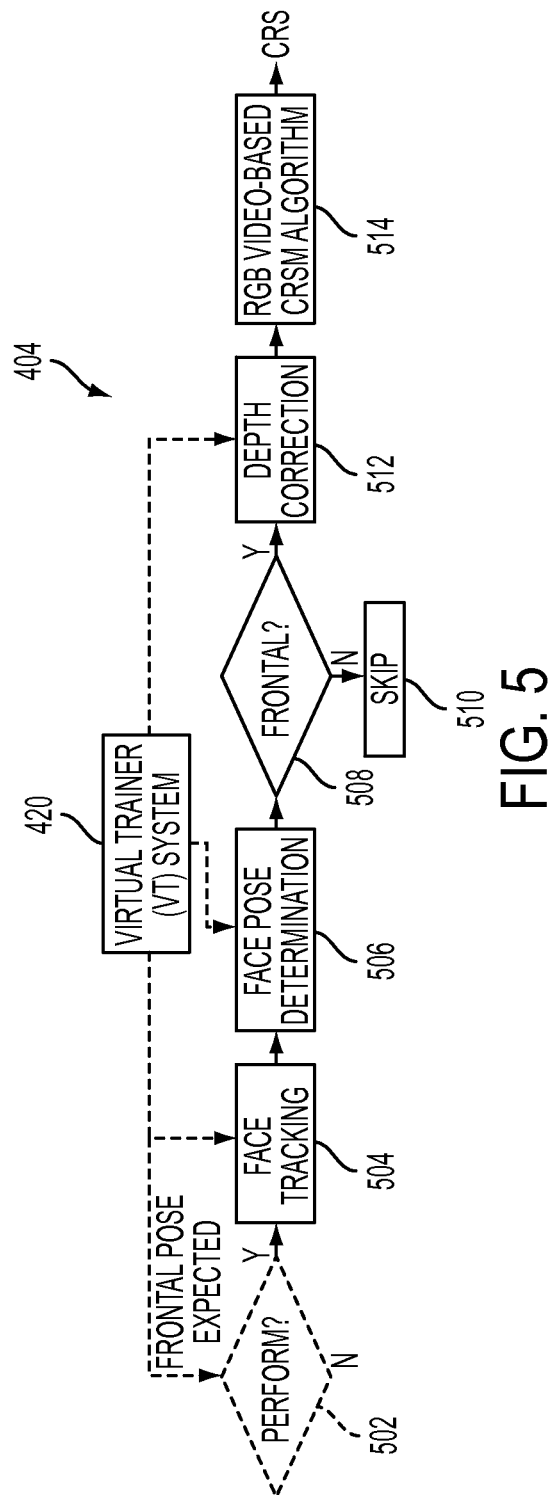
FIG. 5 is a flow chart of a Cardio-Respiratory Signal Monitoring (CRSM) module according to an exemplary embodiment of this disclosure.

FIG. 5 illustrates a flowchart of an exemplary CRSM module 404, where dashed-lines indicate paths that are optional but preferred. The description of the flowchart is as follows:

Given input from a VT system 420 about whether a sufficient segment of exercise, e.g., 3 sec, with frontal pose is expected, the module decides 502 whether to perform the extraction of Cardio-Respiratory Signals (CRS).

If yes, perform face detection and tracking 504. This may be a straightforward output from the VT system if a Kinect® sensor is used; otherwise, many face detection and object tracking algorithms from known arts can be used. If no, skip.

Perform pose estimation 506 to confirm if near-frontal face view 508 is available so that appropriate Region of Interest (ROI) can be selected in order to determine CRS. This may be a straight-forward input from VT. Otherwise, known arts such as that described in X. Zhu, D. Ramanan. "Face Detection, Pose Estimation and Landmark Localization in the Wild", Computer Vision and Pattern Recognition (CVPR) Providence, R.I., June 2012, can be used. If yes, continue. If no, skip 510.

Perform depth correction 512 on the RGB values in the ROI, i.e., section of frontal face of the exerciser. The depth information can come from the VT directly if a Kinect® sensor is used. No correction may be required if CRSM algorithm is robust against distance-attenuation of the RGB signals. If necessary, a candidate correction is a $1/d^2$ correction function since this is a typical model used for illumination-distance modeling.

Perform a CRSM algorithm 514, such as described in one of U.S. Pat. No. 8,617,081, by Mestha et al., issued Dec. 31, 2013 and entitled "Estimating Cardiac Pulse Recovery from Multi-Chanel Source Data via Constrained Source Separation"; U.S. Pat. No. 8,600,213, by Mestha et al., Issued Dec. 3, 2013, and entitled "Filtering Source Video Data via Independent Component Selection"; U.S. Patent Publication No. 2013/0345568, by Mestha et al., published Dec. 26, 2013, and entitled "Video-Based Estimation of Heart Rate Variability"; U.S. Patent Publication No. 2013/0342756, by Xu et al., published Dec. 26, 2013, and entitled "Enabling Hybrid Video Capture of a Scene Illuminated with Unstructured and Structured Illumination Sources"; U.S. Patent Publication No. 2013/0324876, by Bernal et al., published Dec. 5, 2013, and entitled "Processing a Video for Tidal Chest Volume Estimation"; U.S. Patent Publication No. 2013/0322729, by Mestha et al., published Dec. 5, 2013, and entitled "Processing a Video for Vascular Pattern Detection and Cardiac Function Analysis"; U.S. Patent Publication No. 2013/0218028, by Mestha, published Aug. 22, 2013, and entitled "Deriving Arterial Pulse Transit Time from a Source Video Image"; U.S. Patent Publication No. 2013/0077823, by Mestha et al., published Mar. 28, 2013, and entitled "Systems and Methods for Non-Contact Heart Rate Sensing"; U.S. Patent Publication No. 2012/0289850, by Xu et al., published Nov. 15, 2012, and entitled "Monitoring Respiration with a Thermal Imaging System"; and U.S. patent application Ser. No. 13/710,974, by Liu et al., filed Dec. 11, 2012, and entitled "Methods and Systems for Vascular Pattern Localization Using Temporal Features", to extract a snapshot of the CRS and provide this temporal output to Exercise Tracking and Recommendation (ETR) module 402.

It is important to note that relative measurement can be as effective as absolute measurement for purposes of the measurement(s) of physiological metrics as disclosed herein. For example, knowing that a heart rate has increased drastically may provide sufficient evidence for the VT system to issue an alert about the exerciser's condition or to reduce the exertion level as a precaution.

Fall and Lack of Action Detection (FLOAD) Module 406.

Fall detection and lack of action detection is another function that can be readily integrated with the VT system. Fall detection has been well-researched due to its importance for geriatric home care. Early video-based approaches utilize RGB cameras alone, which is more challenging due to the non-uniqueness in converting from 2D image to 3D. More recent works utilize depth information to simplify the task. See Erik E. Stone and Marjorie Skubic, "Evaluation of an Inexpensive Depth Camera for Passive In-Home Fall Risk Assessment," 2011 5th International Conference on Pervasive Computing Technologies for Healthcare (PervasiveHealth) and Workshops.

For purposes of this disclosure, the interest is in modifying/augmenting these known arts to fall detection as well as lack of action detection in the context of exertion level monitoring during a VT setting. It is necessary to differentiate between a fall and mere lack of action such as simply stopping for rest. If a fall is detected, an emergency condition is declared. This may result, for example, in an alert being issued to a caregiver or a security monitor, or notification of the authorities such as by a 911 call. On the other hand, if lack of action is interpreted as merely a resting condition, it may be sufficient to simply stop the VT system and restart when the exerciser is ready. In either case, one option is to transmit an audio-visual message or a phone call to the exerciser to verify that he/she is alright; lack of a reply may result in an emergency response.

Figure 6:
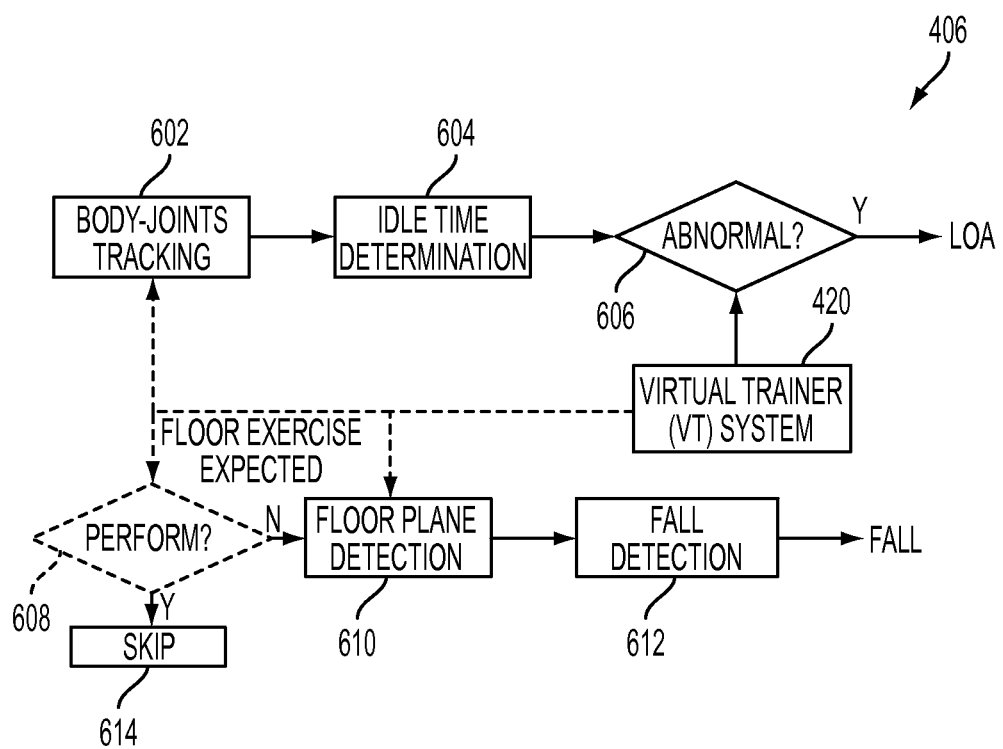
FIG. 6 is a flow chart of a Fall and Lack Of Action Detection (FLOAD) module according to an exemplary embodiment of this disclosure.

FIG. 6 depicts a flowchart of an exemplary FLOAD module 406. In the case of fall detection 612, shown in the lower part of the flowchart, one can re-use known art on fall detection once it is instructed by the VT that the current segment of exercise does not expect a human to lie on the floor 608, otherwise skip 614. However, it may be beneficial to also determine up-front the floor plane 610 before applying known fall detection techniques since in the exercise setting the floor plane can be easily and accurately detected with a simple calibration step, e.g., ask the exerciser to step in and out of the floor area where the exercise will be conducted and use the depth information given by Kinect®. For detecting lack of action (LOA), re-use body-joints tracking 602 available in Kinect® toolset followed by an idle time determination step 604, which can simply be the duration where maximal speed of all joints are below a threshold, i.e., idle. The determined idle time is then compared to the expected idle time provided by the VT system to conclude whether an abnormal LOA 606 has occurred.

Appearance Anomaly Detection (AAD) Module 408.

In the AAD module 408, appearance anomalies such as significant/sudden color change of (facial) skin, abnormal facial expression such as pain, large deviation or abnormal motion compared against the expected motion input by VT, is detected. The goal is to provide early warning of potential injury. The AAD module may share some of the processes in the CRSM 404 and FLOAD 406 modules. For example, tracking of skin color of various body parts, for example facial skin in particular, may use the face tracking and face pose determination in CRSM module to find an appropriate ROI for assessing the facial skin colors. As another example, abnormal motion detection may utilize the body-joints tracking in the FLOAD module to collect the trajectories of those body-joints. These trajectories are then compared to the currently expected trajectories in the VT system to determine whether an abnormal motion has occurred.

Exercise Tracking and Recommendation (ETR) Module 402.

The ETR module 402 is a central control unit that ties an existing VT system 420 with the exertion level and safety inspectors (CRSM, FLOAD, AAD) as previously described. The ETR module can also serve as an exercise advisor which is aware of the exerciser's instantaneous and historical exertion levels. Depending on various information provided from the VT and the exertion level and safety inspectors, the ETR module can determine/recommend the level of difficulty of the exercise in real-time to the VT, alert a third-party to further inspect the situation and respond, and track exercises completed and the corresponding exertion levels extracted by the exertion level inspectors.

Some portions of the detailed description herein are presented in terms of algorithms and symbolic representations of operations on data bits performed by conventional computer components, including a central processing unit (CPU), memory storage devices for the CPU, and connected display devices. These algorithmic descriptions and representations are the means used by those skilled in the data processing arts to most effectively convey the substance of their work to others skilled in the art. An algorithm is generally perceived as a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, as apparent from the discussion herein, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The exemplary embodiment also relates to an apparatus for performing the operations discussed herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the methods described herein. The structure for a variety of these systems is apparent from the description above. In addition, the exemplary embodiment is not described with reference to any particular programming language. It will be appreciated that a variety of programming languages may be used to implement the teachings of the exemplary embodiment as described herein.

A machine-readable medium includes any mechanism for storing or transmitting information in a form readable by a machine (e.g., a computer). For instance, a machine-readable medium includes read only memory ("ROM"); random access memory ("RAM"); magnetic disk storage media; optical storage media; flash memory devices; and electrical, optical, acoustical or other form of propagated signals (e.g., carrier waves, infrared signals, digital signals, etc.), just to mention a few examples.

The methods illustrated throughout the specification, may be implemented in a computer program product that may be executed on a computer. The computer program product may comprise a non-transitory computer-readable recording medium on which a control program is recorded, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other tangible medium from which a computer can read and use. Alternatively, the method may be implemented in transitory media, such as a transmittable carrier wave in which the control program is embodied as a data signal using transmission media, such as acoustic or light waves, such as those generated during radio wave and infrared data communications, and the like.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A computer implemented virtual training (VT) method comprising:
   a VT system electronically communicating via one or both of video and audio instructions for performing an exercise routine to a user of the VT system, the exercise routine to be performed by the user;
   a sensing system sensing exercise motion of the user using one or more sensing elements, the sensing elements including an image capturing device acquiring an image of the user the image capturing system including a tandem depth sensing range camera and a RGB color camera configured to generate a RGBD (Red-Green-Blue-Depth) image of the user;
   an exertion level inspection system processing the image of the user captured by the image capturing device to determine, by an application of animation techniques, an exertion level of the user during performance of the exercise routine, and based on the determined exertion level of the user, the exertion level inspection system performing one of the following optimizations:
   a) visually and/or audibly communicating to the user one or more instructions which increase the user's exertion level;
   b) visually and/or audibly communicating to the user one or more instructions which decrease the user's exertion level; or
   c) visually and/or audibly communicating to the user one or more instructions which maintain the user's exertion levels,
   wherein the method optimizes the user's exertion level by dynamically modifying, the instructions for performing the exercise routine to achieve a determined optimum exertion level of the user.

2. The computer implemented VT method according to claim 1, comprising:
   comparing the sensed exercise motion of the user performing the exercise to a motion associated with the instructions for performing the exercise.

3. The computer implemented VT method according to claim 1, wherein the exertion level of the user is determined using a video-based method to detect one or more physiological metrics associated with the user.

4. The computer implemented VT method according to claim 3, wherein the physiological metrics include one or more cardio-respiratory metrics, respiration rate, heart rate, body temperature and blood pressure.

5. The computer implemented VT method according to claim 1, wherein the method performs two or more of the following:
   performing video-based cardio-respiratory monitoring of the user;
   performing video-based fall and lack of action monitoring of the user; and
   performing video-based appearance anomaly monitoring of the user.

6. The computer implemented VT method according to claim 1,
   wherein the instructions for performing the exercise routine are dynamically modified based on the determined exertion level of the user.

7. The computer implemented VT method according to claim 1, wherein the VT method assesses health data related to the user and uses the health data to determine an appropriate exertion level, and/or the VT method uses an anticipated view of the user, obtained from the prescribed exercise routines, to facilitate measurement of one or more cardio-respiratory metrics associated with the user.

8. The computer implemented VT method according to claim 7, wherein the anticipated view of the user includes any of:
   an expected absolute or relative location, pose, and/or velocity of the face and/or other body parts;
   and the facilitation includes any of:
   improving tracking or localization of the regions of interest of the face and/or other body parts; compensating for the pose changes or velocity of the face and/or other body parts; determining the timing for measuring one or more cardio-respiratory metrics associated with the user; and determining the confidence for the measurement of one or more cardio-respiratory metrics associated with the user.

9. The computer implemented VT method according to claim 1, wherein the image capturing device captures RGB (Red-Green-Blue) data and/or D (Depth) data.

10. The computer implemented VT method according to claim 1, wherein the method comprises performing video-based fall and lack of action monitoring of the user.

11. A virtual training (VT) system comprising:
    a controller configured to execute instructions to perform a virtual training method, and a sensing system including one or more sensing elements operatively associated with the controller, the virtual training method comprising:
    the controller communicating via one or both of video and audio instructions for performing an exercise routine to a user of a VT system, the exercise routine to be performed by the user;
    the sensing system sensing exercise motion of the user using the one or more sensing elements, the sensing elements including an image capturing device acquiring an image of the user the image capturing system including a tandem depth sensing range camera and a RGB color camera configured to generate a RGBD (Red-Green-Blue-Depth) image of the user;
    the controller processing the RGBD image of the user to determine an exertion level of the user during performance of the exercise routine, and based on the determined exertion level of the user, the controller performing one of the following:
    a) visually and/or audibly communicating to the user one or more instructions which increase the exertion level;
    b) visually and/or audibly communicating to the user one or more instructions which decrease the execution level; or
    c) visually and/or audibly communicating to the user one or more instructions which maintain exertion level,
    wherein the method determines an optimum exertion level for the user and dynamically modifies, by the application of animation techniques, the instructions for performing the exercise routine to achieve the optimum exertion level.

12. The VT system according to claim 11, the method comprising:
    comparing the sensed exercise motion of the user performing the exercise to a motion associated with the instructions for performing the exercise.

13. The VT system according to claim 11, wherein the exertion level of the user is determined using a video-based method to detect one or more physiological metrics associated with the user.

14. The VT system according to claim 13, wherein the physiological metrics include one or more cardio-respiratory metrics, respiration rate, heart rate, body temperature and blood pressure.

15. The VT system according to claim 11, wherein the method performs two or more of the following:
performing video-based cardio-respiratory monitoring of the user;
performing video-based fall and lack of action monitoring of the user; and
performing video-based appearance anomaly monitoring of the user.

16. The VT system according to claim 11,
wherein the instructions for performing the exercise routine are dynamically modified based on the determined exertion level of the user.

17. The VT system according to claim 11, wherein the VT method assesses health data related to the user and uses the health data to determine an appropriate exertion level, and/or the VT method uses an anticipated view of the user, obtained from the prescribed exercise routines, to facilitate measurement of one or more cardio-respiratory metrics associated with the user.

18. The computer implemented VT method according to claim 17, wherein the anticipated view of the user includes any of:
an expected absolute or relative location, pose, and/or velocity of the face and/or other body parts;
and the facilitation includes any of:
improving tracking or localization of the regions of interest of the face and/or other body parts; compensating for the pose changes or velocity of the face and/or other body parts; determining the timing for measuring one or more cardio-respiratory metrics associated with the user; and determining the confidence for the measurement of one or more cardio-respiratory metrics associated with the user.

19. The VT system according to claim 11, wherein the image capturing device captures RGB (Red-Green-Blue) data and/or D (Depth) data.

20. The VT system according to claim 11, wherein the method comprises performing video-based fall and lack of action monitoring of the user.

* * * * *